United States Patent
Larson (10) Patent No.: US 10,398,857 B2
(45) Date of Patent: Sep. 3, 2019

(54) PATIENT LINE DISLODGEMENT DETECTION DEVICE AND METHOD

(71) Applicant: Toltec Ventures, LLC, Arvada, CO (US)

(72) Inventor: Byron William Larson, Arvada, CO (US)

(73) Assignee: Toltec Ventures, LLC, Monument, CO (US)

(*) Notice: Subject to any disclaimer, the term of this patent is extended or adjusted under 35 U.S.C. 154(b) by 415 days.

(21) Appl. No.: 15/150,873

(22) Filed: May 10, 2016

(65) Prior Publication Data

US 2017/0014581 A1 Jan. 19, 2017

Related U.S. Application Data

(60) Provisional application No. 62/194,219, filed on Jul. 18, 2015.

(51) Int. Cl.
*A61M 5/168* (2006.01)
*A61M 5/50* (2006.01)
*A61M 5/158* (2006.01)

(52) U.S. Cl.
CPC ...... *A61M 5/5086* (2013.01); *A61M 5/16804* (2013.01); *A61M 5/16831* (2013.01); *A61M 2005/1588* (2013.01); *A61M 2205/14* (2013.01); *A61M 2205/331* (2013.01); *A61M 2205/3331* (2013.01)

(58) Field of Classification Search
CPC ............ A61M 5/16804; A61M 5/5086; A61M 5/16831; A61M 3/0266; A61M 5/1417; A61M 39/281
See application file for complete search history.

(56) References Cited

U.S. PATENT DOCUMENTS

| 4,944,485 A * | 7/1990 | Daoud ................ A61M 39/284 137/560 |
| 5,257,978 A * | 11/1993 | Haber ................. A61M 39/281 251/9 |
| 7,147,615 B2 | 12/2006 | Wariar et al. |
| 8,394,071 B2 | 3/2013 | Howard |
| 2006/0130591 A1 | 6/2006 | Perkins |

(Continued)

OTHER PUBLICATIONS https://web.archive.org/web/20160406050919/http://denyers.com.au/products/anaesthetic-tube-holder/.*

*Primary Examiner* — Bhisma Mehta
*Assistant Examiner* — William R Frehe
(74) *Attorney, Agent, or Firm* — Trenner Law Firm, LLC; Mark D. Trenner (57) ABSTRACT

A patient line dislodgement detection device and method. An example device includes a body having an entrance and an exit. The entrance and the exit are each configured to receive a tubing line therethrough. Applying a force to a tubing line causes the body to restrict fluid flow through the tubing line, thereby indicating a dislodgement condition. An example method includes receiving a tubing line through a dislodgement device. The method also includes restricting fluid flow by the dislodgment device through the tubing line in response to application of a force on the tubing line. The method also includes detecting a dislodgment condition based on restricting the fluid flow through the tubing line.

2 Claims, 8 Drawing Sheets (56) References Cited

U.S. PATENT DOCUMENTS

| | | | |
|---|---|---|---|
| 2006/0169934 A1* | 8/2006 | Werth | A61M 39/284 251/9 |
| 2010/0056976 A1 | 3/2010 | Howard | |
| 2010/0211002 A1* | 8/2010 | Davis | A61M 5/14228 604/67 |
| 2010/0234809 A1* | 9/2010 | Kenley | A61M 39/281 604/180 |
| 2012/0118650 A1* | 5/2012 | Gill | G01G 17/04 177/245 |
| 2012/0215181 A1* | 8/2012 | Lee | A61M 5/16804 604/250 |
| 2017/0021098 A1 | 1/2017 | Rousche et al. | |

\* cited by examiner

PATIENT LINE DISLODGEMENT DETECTION DEVICE AND METHOD

CROSS REFERENCE TO RELATED APPLICATIONS

This application claims the priority benefit of U.S. Provisional Patent Application No. 62/194,219 filed Jul. 18, 2015 for "Needle Dislodgement Detection System and Method," hereby incorporated by reference in its entirety as though fully set forth herein.

BACKGROUND

Intravenous needles are used patients for fluid transfer, such as access to blood for testing (withdrawing blood), drug infusion, fluid nutrition infusion, and saline infusion, to name only a few examples. Other uses of intravenous needles include, but are not limited to, dialysis, other extracorporeal blood processing therapies, and blood transfusions. During use, intravenous needles and/or needle lines are typically secured to the patient via tape or other method. However, if a force is applied to the needle line, such as by the user pulling their arm while the needle line is caught, the needle may become dislodged. Therefore, detection of a dislodged needle is important for patient safety (e.g., to prevent a patient from bleeding to death).

DETAILED DESCRIPTION

A patient line dislodgement detection device and method is disclosed. An example patient line dislodgement detection device includes a body having an entrance and an exit. The entrance and the exit are each configured to receive a tubing line therethrough. Applying a force to a tubing line causes the body to restrict fluid flow through the tubing line, thereby indicating a potential dislodgement condition before the needle is dislodged, which can be implemented to prevent dislodgement.

An example patient line dislodgement detection method includes receiving a tubing line through a dislodgement device. The method also includes restricting fluid flow by the dislodgment device through the tubing line in response to application of a force on the tubing line. The method also includes detecting a dislodgment condition based on restricting the fluid flow through the tubing line.

It takes a certain amount of force to remove a taped needle from a patient's access site. The amount of force the device disclosed herein to restrict the needle line will be less than the force to pull the needle out of the access. This provides a level of engineering predictability that current clinical practice does not have.

In an example, the system and method operates under the force that a patient may apply to a needle line when moving, to cause a restricted flow of fluid to the patient. The restriction may be partial or complete. That is, fluid flow may be partially or completely (i.e., to the point of stopping fluid flow entirely). The restriction, in turn, enables a sensor (e.g., flow and/or pressure sensor(s)) to detect a condition caused by the restriction (e.g., change in flow and/or pressure) prior to the needle becoming dislodged. The condition (e.g., partial and/or complete restriction) may be detected and responded to appropriately.

The restriction may be detected by any suitable means, and is not limited to flow and/or pressure sensor(s). For example, the restriction may be detected by measuring a change in geometric, optical, capacitive, resistive, and/or other property of a component of the needle dislodgement system and/or the fluid caused by a restriction due to the applied force.

In an example, the system and method may implement the applied force to trigger a secondary mechanism which may be utilized for detection of the condition or stoppage of the flow. By way of illustration, a secondary mechanism may include clamping the line so as to reduce or eliminate blood loss from the patient.

Before continuing, it is noted that as used herein, the terms "includes" and "including" mean, but is not limited to, "includes" or "including" and "includes at least" or "including at least." The term "based on" means "based on" and "based at least in part on."

Figure 1:
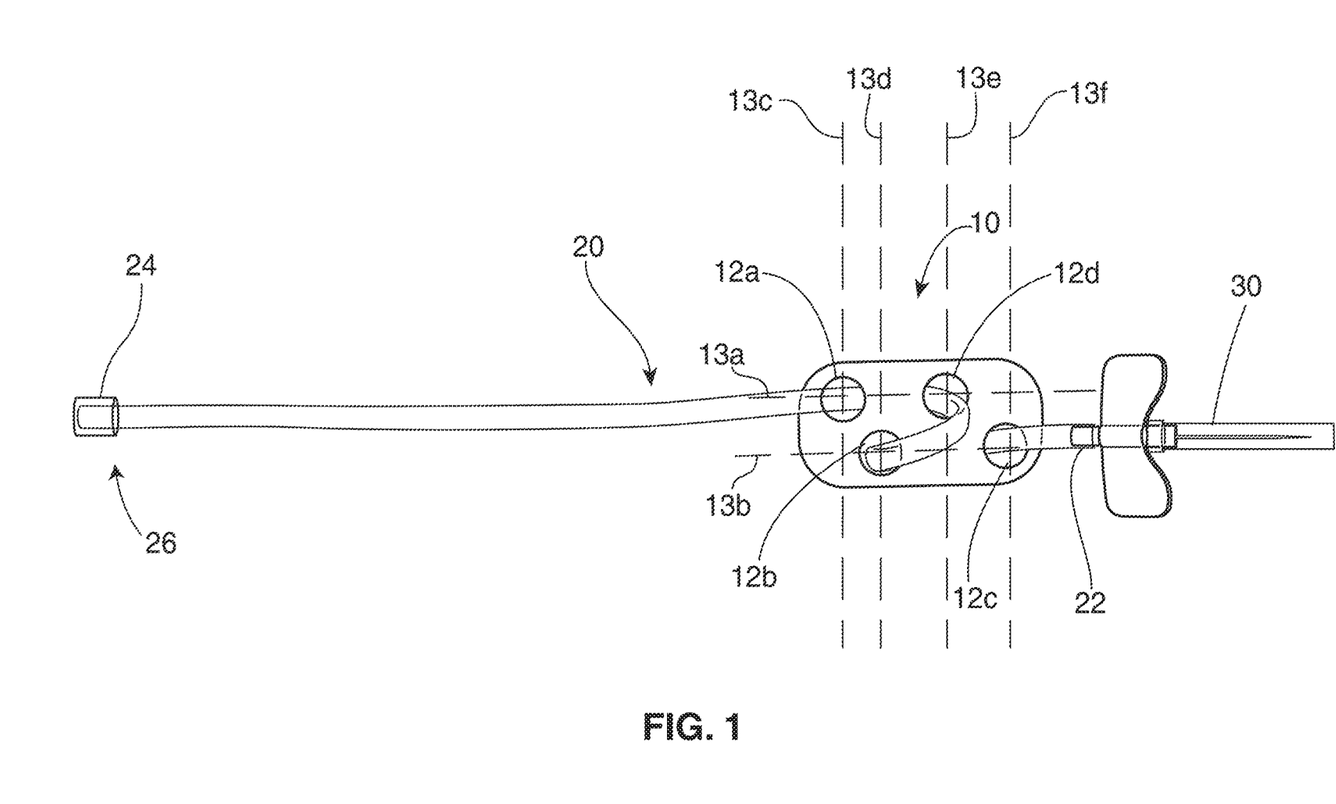
FIG. 1 shows an example patient line dislodgement detection device.

FIG. 1 shows an example patient line dislodgement detection device. In this example, the device 10 includes a body having openings 12a-d. The openings 12a-d are configured to receive a tubing line 20 for a patient. In an example, the tubing line 20 may be connected to a needle 30 (shown encased in a cover or shield) on one end 22 of the tubing line 20 and a fluid supply connection 24 on the other end 26 of the tubing line 20. By way of non-limiting illustration, the needle can be an intravenous needle. However, other needles for applying or retrieving other types of fluids to a patient may also be used.

It is noted that the device 10 is illustrative of an example configuration. The device 10 may have any suitable configuration, and is not limited to the configuration shown. Other configurations will be readily apparent to those having ordinary skill in the art after becoming familiar with the teachings herein.

The device 10 may be used with any patient line, such as lines to infuse fluid to and/or retrieve fluid from a human or veterinary patient. The device can similarly be applied to fluid connections to catheters for infusing or extracting fluids. In an example, a needle is attached to tubing line to extract or infuse fluids. These fluid lines are often attached to pumps, fluid bags, tees, and/or other connectors. Example fluids are blood, medications, saline, irrigation fluids, air (including suction), gases other than air, and nutritional products.

Figure 2:
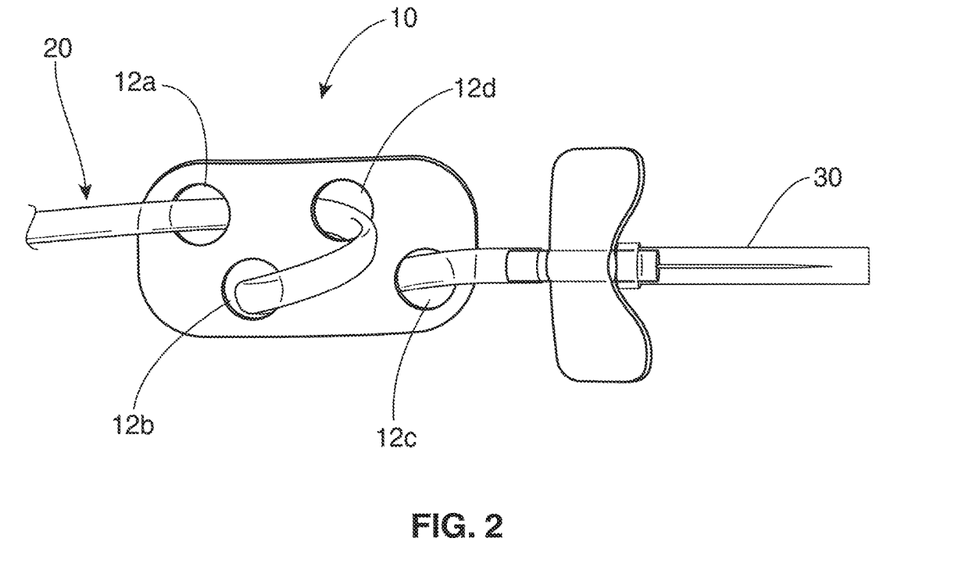
FIG. 2 is a close-up view of the example patient line dislodgement detection device of FIG. 1.

FIG. 2 is a close-up view of the example patient line dislodgement detection device 10 of FIG. 1. The patient line dislodgement detection device 10 is shown as it may include a body having an entrance and an exit. In an example, the entrance and the exit is formed by the openings 12a-d configured to receive a tubing line therethrough. Applying a force to the tubing line 20 (e.g., by pulling) causes the body to tighten within the openings (see, e.g., the illustration of FIGS. 3 and 4 described below) and restrict fluid flow through the tubing line 20, thereby indicating a dislodgement condition.

In an example, the body is generally rectangular shaped, although other shapes, sizes, and configurations may also be provided. The body has a first opening 12a forming the entrance and a second opening 12c forming the exit. A third opening 12d and a fourth opening 12b reverse the direction of the tubing 20.

In an example, the first opening 12a and the third opening 12d are formed in the body along a first threading line 13a. The second opening 12c and fourth opening 12b are formed in the body along a second threading line 13b. The first threading line 13a may be spaced apart from the second threading line 13b. The first threading line 13a may be substantially parallel to the second threading line 13b.

The first opening 12a may be offset from the fourth opening 12b, as shown by lines 13c and 13d in FIG. 2. In addition, the second opening 12c may be offset from the third opening 12d, also as shown by lines 13e and 13f in FIG. 2. However, this configuration is not required in all examples.

In an example, the tubing line 20 is threaded over a first (e.g., top) side of the body and through the first opening 12a to a second (e.g., bottom) side of the body. The tubing line 20 is further threaded from the second side of the body through the third opening 12d to the second side of the body. The tubing line 20 is further threaded from the first side of the body through the fourth opening 12b to the second side of the body. The tubing line 20 is further threaded from the second side of the body through the second opening 12c to the first side of the body.

In an example use case, the line 20 may be pulled, such as may happen when the patient moves and dislodges the needle from a blood vessel. When the line 20 is pulled through the openings 12a-d, flow is at least partially restricted, if not fully blocked through the line 20. It is this restriction which can be detected using any suitable sensor or other detection device, such as but not limited to pressure and/or flow sensor(s).

As such, the device 10 enables enhanced detection of needle dislodgement. A dislodged needle can result in inappropriate fluid delivery (for example, inadequate drug delivery), fluid loss (for example, blood loss resulting in patient death), or inappropriate fluid extraction (for example, extraction of ambient air instead of a patient fluid).

Figure 3:
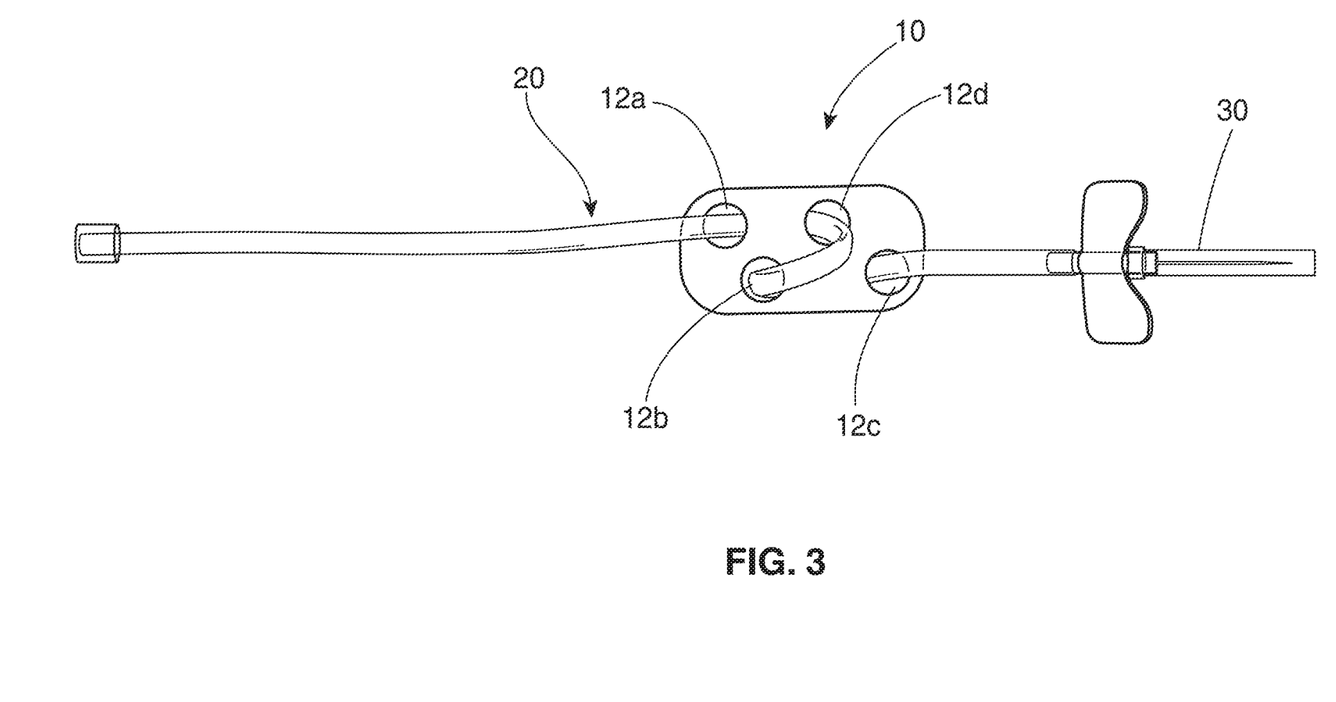
FIG. 3 shows an example patient line dislodgement detection device in an unrestricted configuration.
Figure 4:
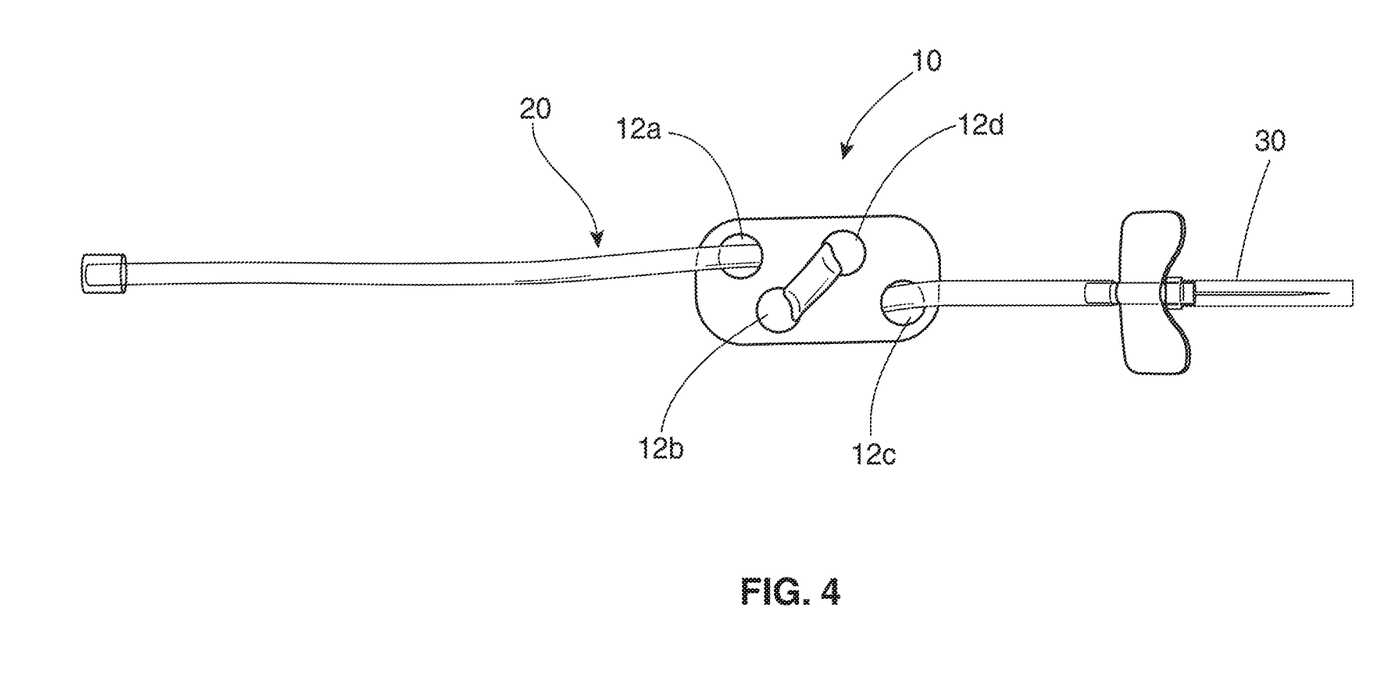
FIG. 4 shows an example patient line dislodgement detection device in a restricted configuration illustrating a dislodgement condition.
Figure 5:
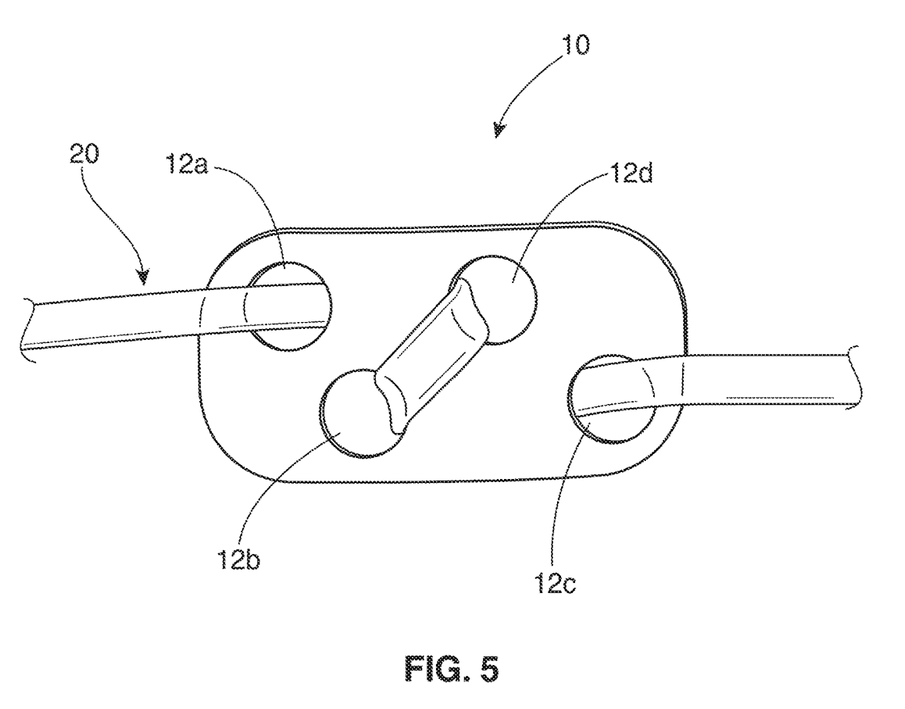
FIG. 5 is a close-up view of the example patient line dislodgement detection device of FIG. 4.

FIG. 3 shows an example patient line dislodgement detection device in an unrestricted configuration. FIG. 4 shows an example patient line dislodgement detection device in a restricted configuration illustrating a dislodgement condition. FIG. 5 is a close-up view of the example patient line dislodgement detection device of FIG. 4.

The patient line dislodgement detection method is based at least in part on the force on a needle line that might dislodge a needle or otherwise restrict the fluid flow. An example force may be a patient that inadvertently tugs on the fluid delivery line. The force is converted by the device to a means of restricting the needle line. The means may be a restricted line, a completely occluded line, or a valve that partially occludes after application of the aforementioned force. Other means are also contemplated. This fluid restriction provides needle dislodgement detection via a secondary sensing method. For example, pressure monitoring of the fluid infusion line, flow rate monitoring in the fluid infusion line, and/or other sensing that measures geometric changes due to the applied force.

An example patient line dislodgement detection method includes receiving a tubing line through a dislodgement device. The example method also includes restricting fluid flow by the dislodgment device through the tubing line in response to application of a force on the tubing line. The example method also includes detecting a dislodgment condition based on restricting the fluid flow through the tubing line. The example method also includes the dislodgment device restricting fluid flow in a needle line connected to a needle, catheter, or patient fluid connection.

In an example, the force at least partially restricts fluid flow in the tubing line. In another example, the force directly occludes the tubing line to completely stop fluid flow through the tubing line. Accordingly, the method includes measuring a physical change caused by partially or fully restricting the fluid flow. For example, measuring may include at least one of pressure sensing, flow rate sensing, and other restriction sensing caused by a strain on the tubing line 20. Measuring the physical change of the tubing line 20, the body, and/or the fluid in the tubing line 20 may include at least one of geometric, optical, capacitive, or resistive physical properties.

It is noted that at least partially (or fully) restricting the fluid flow may be by the body itself, and/or by a secondary device. Example secondary devices may include, but are not limited to a line clamp, a needle protection sheath, a wing, and an integral component of the tubing line.

Figure 6A:
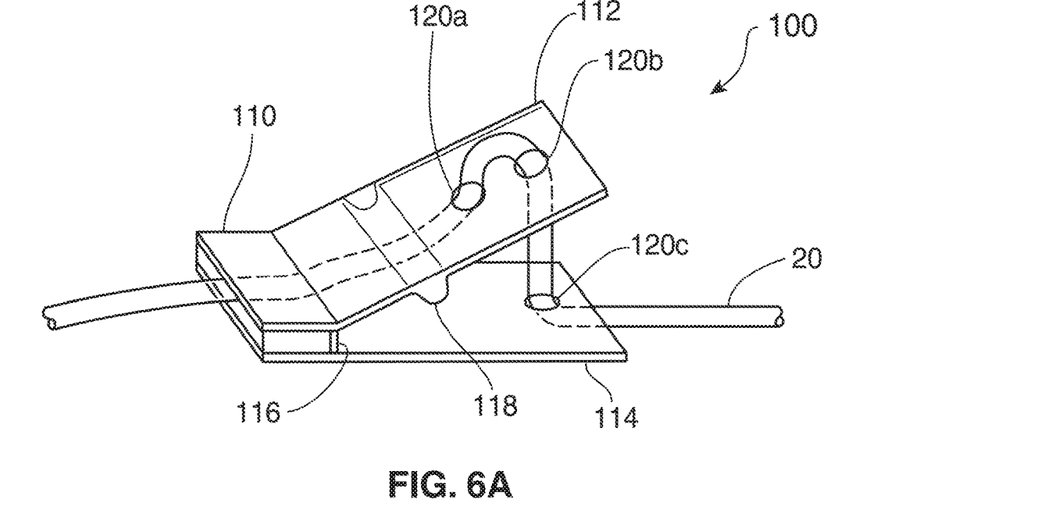
FIGS. 6A-6B show another example patient line dislodgement detection device.
Figure 6B:
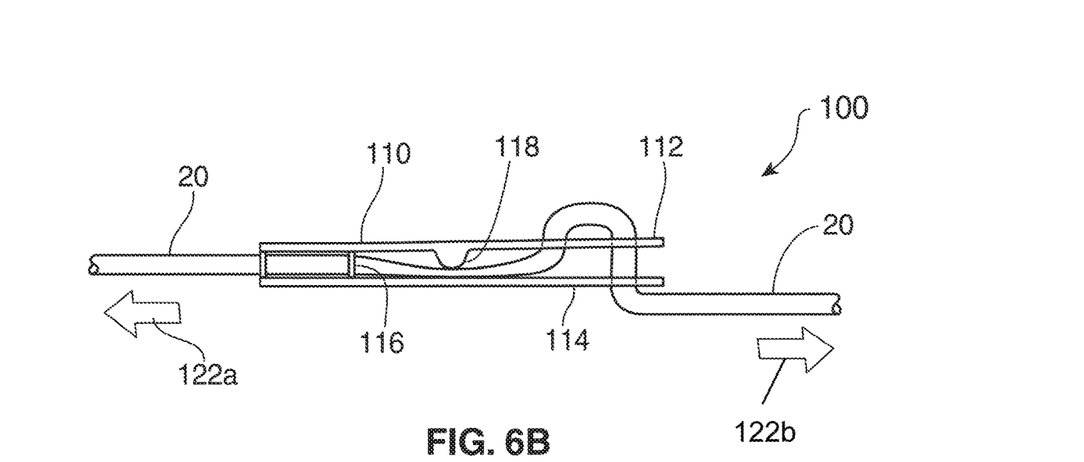

FIGS. 6A-6B show another example patient line dislodgement detection device 100. The example patient line dislodgement detection device 100 includes a body 110 having an entrance and an exit. The entrance and the exit are each configured to receive a tubing line 20 therethrough. Applying a force to the tubing line 20 causes the body 110 to restrict fluid flow through the tubing 20 line, thereby indicating a dislodgement condition, as already described above.

In an example, the body 110 has a first plate 112 and a second plate 114. The first plate 112 is connected by a hinge 116 to the second plate 114. A restriction tab 118 is formed on the first plate 112 (although it may be formed on the second plate 114 or both plates 112 and 114).

The tubing line 20 may be threaded through an entrance (e.g., formed through the hinge 116) into a first opening 120a in the first plate 112. The tubing line 20 is further threaded through a second opening 120b in the first plate 112, and through the exit (e.g., formed as an opening 120c in the second plate 114).

Applying the force to the tubing line 20 (e.g., in the direction of arrow 122a and/or arrow 122b) closes the first plate 112 against the second plate 114. This closure causes the restriction tab 118 to pinch the tubing line 20 between the first plate 112 and the second plate 114, as shown in FIG. 6B and thereby partially or fully restrict flow through the tubing line 20.

Figure 7A:
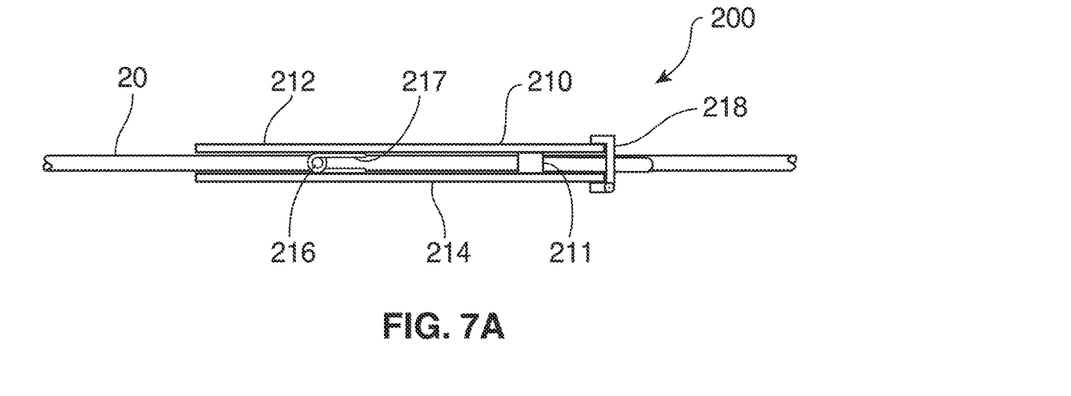
FIGS. 7A-7C show another example patient line dislodgement detection device.
Figure 7B:
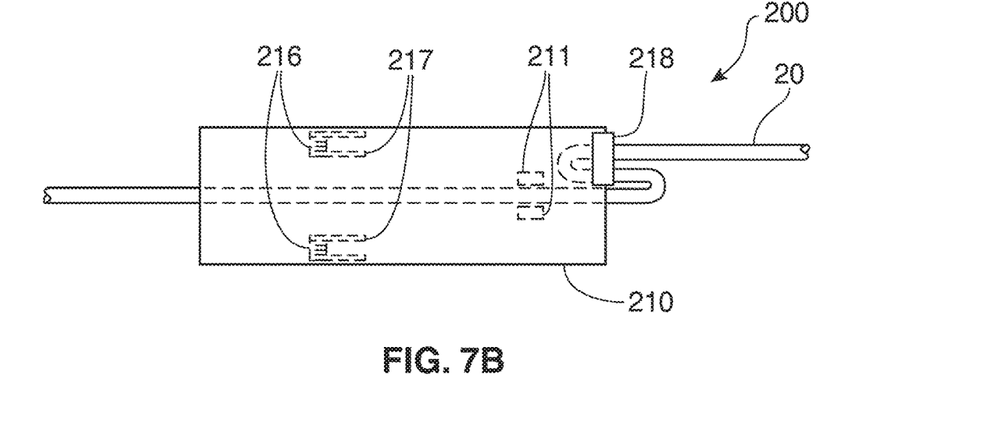
Figure 7C:
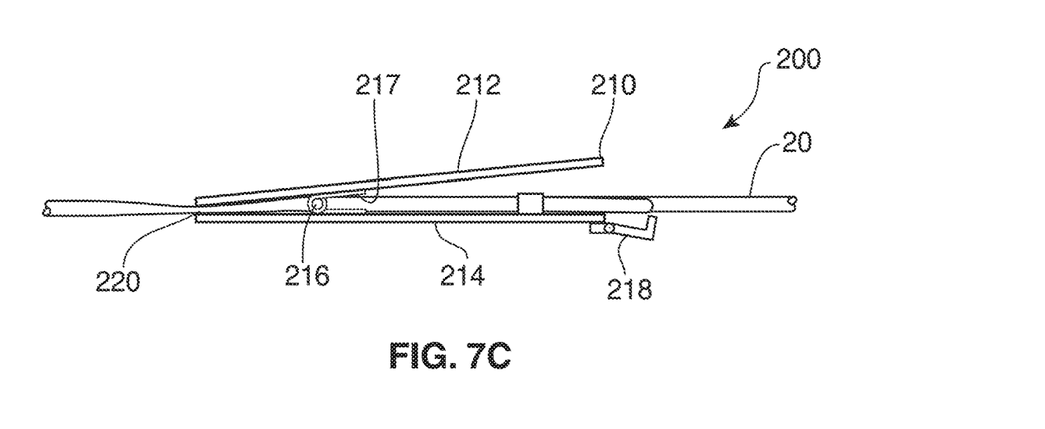

FIGS. 7A-7C show another example patient line dislodgement detection device 200. The example patient line dislodgement detection device 200 includes a body 210 having an entrance and an exit. The entrance and the exit are each configured to receive a tubing line 20 therethrough. A guide and/or spacer 2 is provided to support the tubing line 20. Applying a force to the tubing line 20 causes the body 210 to restrict fluid flow through the tubing line, thereby indicating a dislodgement condition as already discussed above.

In an example, the body 210 has a first plate 212 and a second plate 214. The first plate 212 is connected by one or more hinge 216 to the second plate 214. One or more spring member 217 biases the hinge(s) 216 in an open position. A trigger member 218 is hinged on either first plate 212 or the second plate 214 (as shown in FIG. 7A), and removably grasps the other plate to hold the first plate 212 generally parallel to the second plate 214 against a bias of the spring member 217.

Applying a force to the tubing line 20 pulls against and releases the trigger member 218. Releasing the trigger member 218 causes the first plate 212 and the second plate 214 to close under bias of the spring member 217. This action pinches the tubing line 20, e.g., at a vertex 220 formed between the first plate 212 and the second plate 214.

Figure 8:
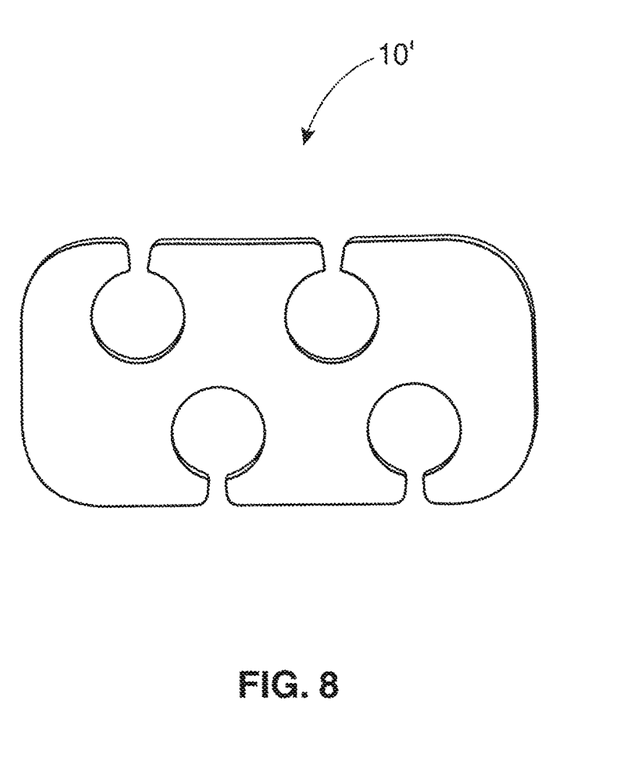
FIG. 8 shows another example patient line dislodgement detection device.

FIG. 8 shows another example patient line dislodgement detection device 10'. In this example, the device 10' includes a body having slotted openings (corresponding to openings 12a-d of device 10). The openings are configured to receive a tubing line (not shown) for a patient and operates similar to the device 10 already described above. The slotted openings enable insertion of a tubing line without having to thread the tubing line through the holes (e.g., the tubing line can be inserted through the slots. That is, the device 10' can be attached to the needle line after the needle line is manufactured (for example, at the clinic), and the "keyhole" slots can provide easy attachment but will still inhibit removal of the tube from the device thereby enabling it to operate as described above for device 10.

It is noted that the examples shown and described are provided for purposes of illustration and are not intended to be limiting. Still other examples are also contemplated.

The invention claimed is:

1. A patient line dislodgement detection device, comprising: a body having a first plate and a second plate, the first plate connected to the second plate by a hinge; wherein the hinge has an entrance and the second plate has an exit; wherein a restriction tab is formed on the first plate; wherein a tubing line is threaded through the entrance formed in the hinge, into a first opening in the first plate, the tubing line further threaded through a second opening in the first plate and through the exit formed as an opening in the second plate; wherein applying a force to the tubing line pulls the first plate toward the second plate and causes the restriction tab to pinch the tubing line between the first plate and the second plate, thereby restricting fluid flow through the tubing line and indicating a dislodgment condition.

2. A patient line dislodgement detection device, comprising: a body having a first plate and a second plate; wherein the body has an entrance and an exit; wherein the first plate is connected to the second plate by a hinge and a spring member; wherein a trigger member holds the first plate generally parallel to the second plate against a bias of the spring member; wherein the entrance and the exit are each configured to receive a tubing line therethrough; wherein applying a force to the tubing line releases the trigger member and causes the first plate and the second plate to pinch the tubing line under the bias of the spring member, thereby restricting fluid flow through the tubing line and indicating a dislodgement condition.

* * * * *